(12) United States Patent
Halkos et al.

(10) Patent No.: US 10,149,672 B2
(45) Date of Patent: Dec. 11, 2018

(54) DEVICES AND METHODS FOR STABILIZING TISSUE

(71) Applicant: Emory University, Atlanta, GA (US)

(72) Inventors: Michael Halkos, Decatur, GA (US); Sai Muralidhar Padala, Atlanta, GA (US)

(73) Assignee: Emory University, Atlanta, GA (US)

( * ) Notice: Subject to any disclaimer, the term of this patent is extended or adjusted under 35 U.S.C. 154(b) by 153 days.

(21) Appl. No.: 15/199,136

(22) Filed: Jun. 30, 2016

(65) Prior Publication Data

US 2017/0000508 A1 Jan. 5, 2017

Related U.S. Application Data

(60) Provisional application No. 62/186,716, filed on Jun. 30, 2015.

(51) Int. Cl.
*A61F 2/00* (2006.01)
*A61B 17/02* (2006.01)
*A61B 17/30* (2006.01)
*A61B 17/00* (2006.01)
*A61B 90/50* (2016.01)

(52) U.S. Cl.
CPC ...... *A61B 17/0218* (2013.01); *A61B 17/0206* (2013.01); *A61B 2017/00243* (2013.01); *A61B 2017/00566* (2013.01); *A61B 2017/0243* (2013.01); *A61B 2017/308* (2013.01); *A61B 2090/508* (2016.02)

(58) Field of Classification Search
CPC . A61B 17/02; A61B 17/0206; A61B 17/0218; A61B 2017/00243; A61B 17/30

USPC ......................................................... 600/37
See application file for complete search history.

(56) References Cited

U.S. PATENT DOCUMENTS

| 6,394,951 | B1 | 5/2002 | Taylor et al. |
| 6,464,629 | B1 * | 10/2002 | Boone ................... A61B 17/02 600/37 |
| 6,743,169 | B1 | 6/2004 | Taylor et al. |
| 6,758,809 | B2 | 7/2004 | Briscoe et al. |
| 7,311,664 | B2 | 12/2007 | Goodman et al. |
| 7,338,434 | B1 * | 3/2008 | Haarstad .......... A61B 17/00234 600/201 |
| 7,399,272 | B2 | 7/2008 | Kim et al. |
| 7,476,196 | B2 | 1/2009 | Spence et al. |
| 7,503,891 | B2 | 3/2009 | Green, II et al. |
| 7,585,277 | B2 | 9/2009 | Taylor et al. |
| 7,794,387 | B2 | 9/2010 | Olson et al. |

(Continued)

*Primary Examiner* — John Lacyk
(74) *Attorney, Agent, or Firm* — Emory Patent Group

(57) ABSTRACT

The devices and methods relate to devices for stabilizing and/or positioning tissue (e.g., heart) within a surgical area. The device may include an articulating arm and a tissue stabilizing member. The device may include one or more stabilizing segments disposed along at least a portion of the length of the articulating arm. Each stabilizing segment may be configured to compress and expand with respect to an internal channel of the arm. The articulating arm may be configured to move between a fixed state and movable state based on a state of the one or more stabilizing segments. In the fixed state, the one or more stabilizing segments may be compressed against the internal channel. In the movable state, the one or more stabilizing segments may be expanded with respect to the internal channel.

20 Claims, 9 Drawing Sheets

(56) References Cited

U.S. PATENT DOCUMENTS

| | | |
|---|---|---|
| 8,460,172 B2 | 6/2013 | Meyer et al. |
| 2003/0083555 A1* | 5/2003 | Hunt ............... A61B 17/02 |
| | | 600/229 |
| 2003/0229271 A1 | 12/2003 | Briscoe et al. |
| 2004/0116897 A1 | 6/2004 | Aboul-Hosn |
| 2005/0215851 A1* | 9/2005 | Kim ............... A61B 17/02 |
| | | 600/37 |
| 2010/0041942 A1 | 2/2010 | Okada |
| 2012/0078061 A1 | 3/2012 | Calafiore et al. |
| 2012/0157788 A1 | 6/2012 | Serowski et al. |

* cited by examiner

DEVICES AND METHODS FOR STABILIZING TISSUE

CROSS REFERENCE TO RELATED APPLICATIONS

This application claims priority to U.S. Provisional Application No. 62/186,716 filed Jun. 30, 2015. The entirety of this application is hereby incorporated by reference for all purposes.

BACKGROUND

Coronary artery bypass surgery (CABG) is one of the most commonly performed surgeries in the United States by cardiothoracic surgeons. One common coronary bypass surgery procedure involves connecting the left internal mammary artery (LIMA) to the left descending coronary artery (LAD), in order to restore proper blood flow to the left ventricle. To conduct these reconnections minimally invasive, special instruments and devices are required. These instruments and devices include a device capable of stabilizing and positioning the heart, so that the surgeon can attach and reconnect the delicate coronary arteries. However, current devices capable of stabilizing and positioning the heart are generally too big and/or bulky making them difficult to efficiently and accurately position the devices with respect to the heart in the confined space provided by minimally invasive surgery.

SUMMARY

Thus, there is a need for tissue stabilizing devices and methods that are structured for improved positioning within the surgical area. Specifically, there is a need for device having a reduced size and bulk while providing increased flexibility.

The disclosure relates to devices and methods for stabilizing and/or positioning tissue (e.g., heart) within a surgical area. In some embodiments, the device may include an articulating arm having a first end, a second end, and a length there between. The device may further include one or more channels disposed along at least the length of the articulating arm. The one or more channels may include an internal channel disposed along at least the length of the articulating arm. The device may further include one or more stabilizing segments disposed along at least a portion of the length of the articulating arm. Each stabilizing segment may be configured to compress and expand with respect to the internal channel. In some embodiments, the device may include a plurality of ports disposed on the internal channel within each stabilizing segment. The device may further include a tissue stabilizing member disposed at the second end of the articulating arm.

In some embodiments, the articulating arm may be configured to move between a fixed state and movable state based on a state of the one or more stabilizing segments. In the fixed state, the one or more stabilizing segments may be compressed against the internal channel. In the movable state, the one or more stabilizing segments may be expanded with respect to the internal channel.

In some embodiments, the device may include an articulating arm having a first end, a second end, and a length there between. The device may further include one or more channels disposed along at least the length of the articulating arm. The one or more channels may include an internal channel disposed along at least the length of the articulating arm. In some embodiments, the device may further include one or more stabilizing segments disposed along at least a portion of the length of the articulating arm. Each stabilizing segment may be configured to compress and expand with respect to the internal channel. In some embodiments, the device may include a plurality of stabilizing particles disposed within each stabilizing segment. The device may further include a tissue stabilizing member disposed at the second end.

In some embodiments, the articulating arm may be configured to move between a fixed state and movable state based on a state of the one or more stabilizing segments. In the fixed state, the one or more stabilizing particles may be compressed against the internal channel by the one or more stabilizing segments. In the movable state, the one or more stabilizing particles may be released within each stabilizing segment by the one or more stabilizing segments being expanded with respect to the internal channel.

In some embodiments, the device may include one or more articulating segments disposed between the one or more stabilizing segments along the length of the articulating arm. In some embodiments, the one or more articulating segments and the stabilizing segments may be disposed along a portion of the length of the articulating arm and are disposed to surround the internal channel.

In some embodiments, the device may include a connection member disposed between the articulating arm and the tissue stabilizing member. The tissue stabilizing member and the articulating arm may be configured to rotate independently with respect to the connection member. In some embodiments, the device may include a locking member disposed on the connection member and configured to independently lock a position of the tissue stabilizing member and a position of the articulating arm with respect to the connection member. In some embodiments, the connection member may include a first section connected to the articulating arm, a second section connected to the tissue stabilizing member and a rotation member disposed within the first section and the second section.

In some embodiments, the device may include a tissue stabilizing member. The device may further include an articulating arm having a first end, a second end, and a length there between. The tissue stabilizing member may be disposed on one of the ends. In some embodiments, the tissue stabilizing member may include a first segment and an opposing second segment, the first segment and the second segment being configured to be moved independently. In some embodiments, the first and second segments may include a plurality of tissue contact members.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DETAILED DESCRIPTION OF THE EMBODIMENTS

Figure 1:
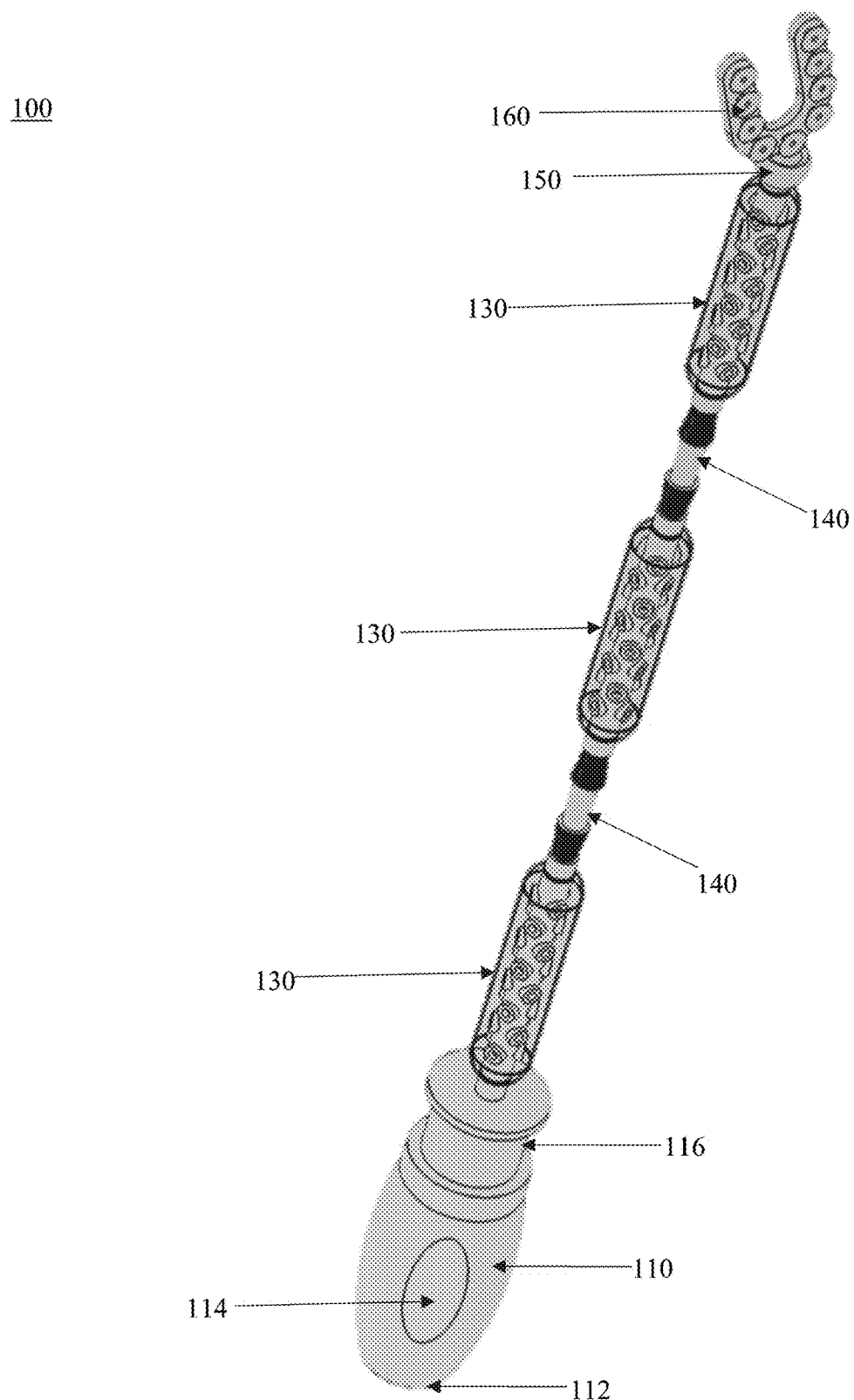
FIG. 1 shows a device for stabilizing tissue according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications.

The terms "distal" and "proximal" used herein with respect to the device and features are with respect to the position of the device when in use. "Distal" indicates an end of the device or a feature of the device closest to, or a direction towards the treatment site, and "proximal" indicates an end of the device or a feature of the device farthest from, or a direction away from the treatment area. "Treatment area" refers to any site or region of a subject, human or animal, intended to be treated, such as a tissue of an organ or muscle. Although the treatment area is discussed with respect to stabilizing and/or positioning a heart within the thoracic cavity, it will be understood that the treatment area may be other regions, for example, other anatomic spaces or cavities containing body tissue.

The disclosed devices and methods are described with respect to stabilizing and/or positioning the heart within the thoracic cavity, for example to perform a medical procedure, such as cardiac surgery (e.g., CABG procedures, heart valve repair/replacement, revascularization, ablation, etc.). However, it will be understood that the devices and methods may be used with other medical procedures (other diagnostic and/or therapeutic procedures such as delivery of therapeutic agents, lead placement, biopsy, etc.) and/or other areas.

In some embodiments, the device may include an articulating arm and a tissue stabilizing member disposed at one end of the articulating arm and configured to engage a treatment area (e.g., heart tissue). The articulating arm may be configured to position the tissue stabilizing member relative to the treatment area (e.g., tissue). The articulating arm may include one or more stabilizing segments disposed along the length of the arm. In some embodiments, the arm may be configured to move between a fixed state or movable state based on a state of the one or more stabilizing segments. By way of example, the articulating arm may be in a fixed state when each segment is in a rigid or locked state (e.g., hard to move/articulate the one or more segments with respect to the tissue stabilizing member and/or treatment area) and in movable state when the one or more stabilizing segments are in a released or expanded state (e.g., easier to move/articulate the one or more segments with respect to the tissue stabilizing member and/or treatment area). The articulating arm may include a handle member disposed at the other end of the articulating arm. The device may also include a connection member that is disposed between the articulating arm and the tissue stabilizing member.

FIGS. 1-9 show examples of articulating arms, tissue stabilizing members, connection members, and/or handle members according to embodiments. However, it will be understood that the systems are not limited to the configuration and/or combination of the articulating arm, tissue stabilizing members, connection members, and handle members as shown in and described with respect the figures. The systems may include any combination of the embodiments of, omit, and/or use alternatives for any of the articulating arms, tissue stabilizing members, connection members, and/or handle members.

The disclosed devices can provide additional flexibility of the articulating arm to allow for improved positioning of the tissue stabilizing member. This can be particularly for useful for variation in patient anatomy, such as left anterior descending anatomy. The disclosed devices are also structured to have a shorter arm and smaller size than conventional devices while providing additional flexibility of the articulating arm. Therefore, the disclosed devices can reduce the crowding in the surgical work space and require smaller incisions for use.

In some embodiments, the tissue stabilizing device may include an articulating arm that includes one or more stabilizing segments that are configured to be expanded (or released) and compressed. For example, when the one or more stabilizing segments are expanded, for example, by supplying air from a vacuum source, the segment and/or arm may be in a movable state. In this example, when the stabilizing segments are compressed, for example, by removing air using a vacuum source, the segment and/or arm may be in a fixed state. FIGS. 1-3 and 9 show examples of a tissue stabilizing device including an articulating arm having one or more stabilizing segments according to some embodiments.

FIGS. 1-5 show views of a tissue stabilizing device 100 according to some embodiments. As shown in these figures, the tissue stabilizing device 100 may include a handle member 110 disposed at the first (proximal) end, a tissue stabilizing member 160 disposed at the second (distal) end and an articulating arm 120 disposed between the handle member 110 and the tissue stabilizing member 160.

In some embodiments, the device 100 may include a connection member 150 disposed between the arm 120 and the tissue stabilizing member 160. The connection member 150 may mechanically and fluidly connect the arm 120 and the tissue stabilizing member 160. In some embodiments, the arm 120 and the tissue stabilizing member 160 may be configured to move independently with respect to each other and/or the connection member 150. In some embodiments, the connection member 150 may include but is not limited to a ball joint.

Figure 2:
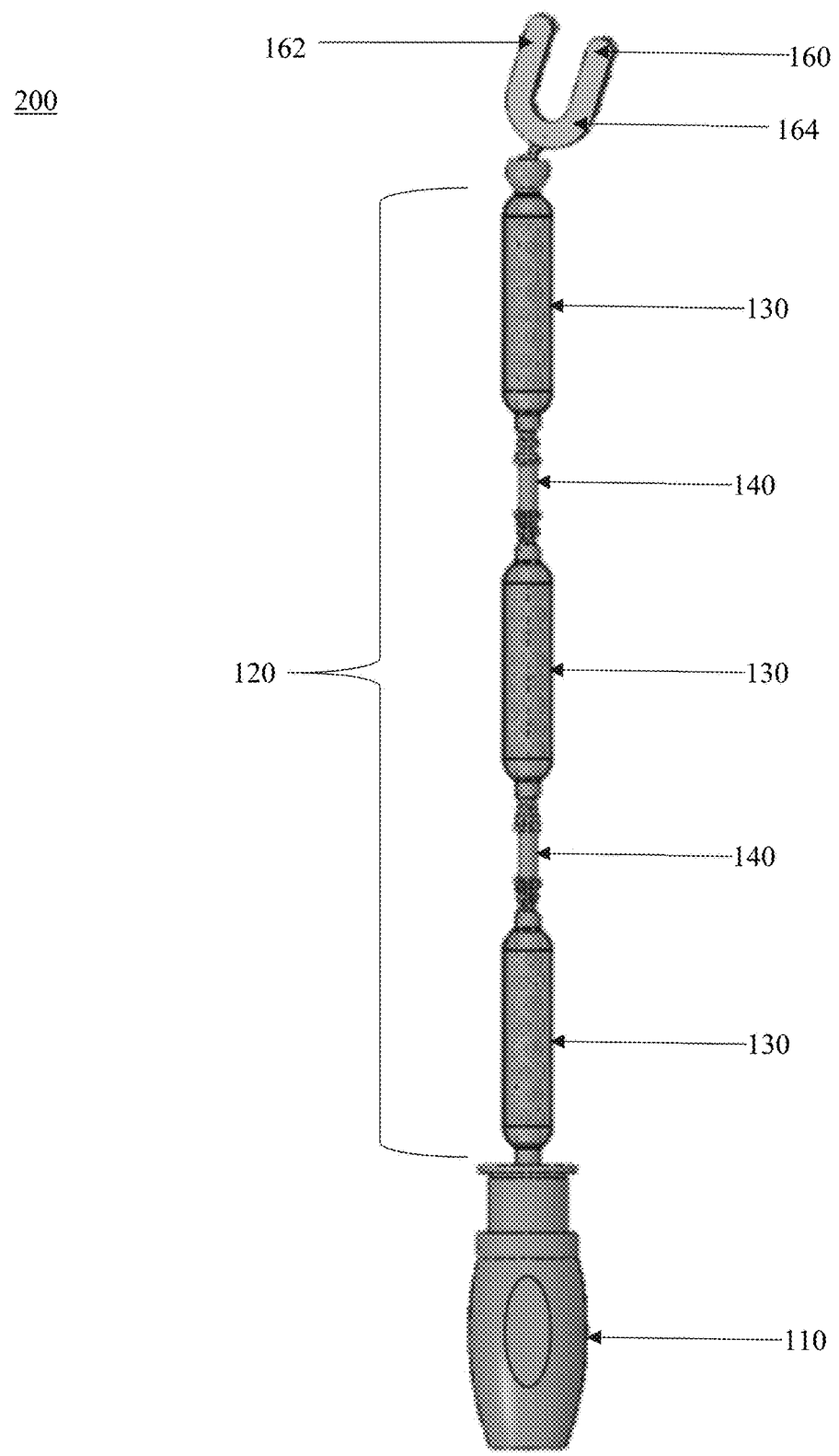
FIG. 2 shows another view of the device shown in FIG. 1.
Figure 3:
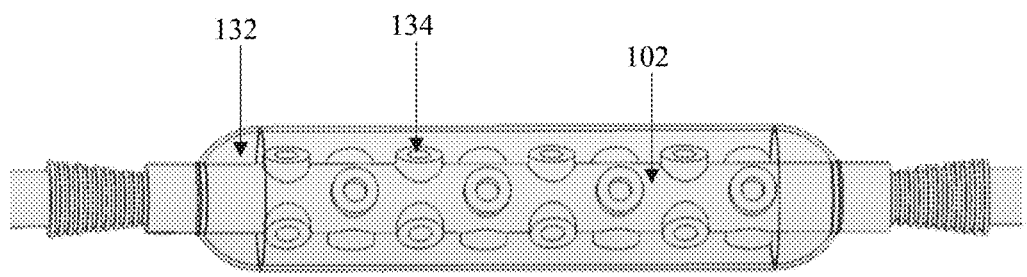
FIG. 3 shows an enlarged partial view of the device shown in FIG. 1.

In some embodiments, the tissue stabilizing device 100 may include one or more channels or lumens. As shown in FIGS. 1-3, the device 100 may include a channel 102 that extends at least along the length of the handle member 110 and the arm 120. The channel 102 may be configured to communicate and/or connect to at least a vacuum source. In some embodiments, the proximal, the open end of the handle 110 may act as an inlet for at least the vacuum source and communicate with the one or more of the channels including the channel 102.

In some embodiments, the device 100 may include one or more additional and/or alternative channels. For example, the device 100 may include one or more channels that extend only within the length of the arm 120. For example, the one or more internal channels may terminate at a connection member 150 that connects the arm 120 and the stabilizing member 160. In some embodiments, the device may include one or more channels that extend between the handle member 110 and the tissue stabilizing member 160. In some embodiments, the device may include one or more channels configured to receive a suspension that is configured to control the position of the arm 120 and/or the tissue stabilizing member 160 with respect to the handle member 110 and/or the treatment area.

In some embodiments, the device 100 may include one or more channels configured to communicate and/or connect to at least a vacuum source to deliver vacuum pressure to the tissue stabilizing member 160. In some embodiments, the connection member 150 may include one or more channels that communicates with the one or more channels of the arm 120 so as to deliver vacuum pressure to the tissue stabilizing member 160. In some embodiments, the connection member 150 may include a vacuum connection configured to connect a vacuum source and/or deliver vacuum pressure from a vacuum source to the tissue stabilizing member 160.

In some embodiments, the handle member 110 may include a rotating portion 112 configured to allow movement of the arm 120 and/or the tissue stabilizing member 160 with respect to the treatment area. In some embodiments, the rotating portion 112 may include one or more grip portions 114 disposed along the circumference of the rotating portion 112. By way of example, a physician may position the tissue stabilizing member 160 with respect to the treatment area by gripping the one or more grip portions 114 and rotating the rotating portion 112.

In some embodiments, the handle member 110 may include a mounting member 116 configured to rigidly fix the tissue stabilizing device 100 to a stationary member, such as a sternal retractor, an operating table, ceiling, floor or other relatively immovable objects. In some embodiments, the handle member 110 may also include a locking member (not shown) configured to lock the position of the arm 120 and/or the position of the tissue stabilizing member 160 with respect to the handle member 110 and/or the treatment area.

In some embodiments, the arm 120 may include one or more stabilizing segments 130 disposed along the length of the arm. In some embodiments, the one or more stabilizing segments 130 may be configured to change between a movable state and a fixed (or stabilizing) state. In the movable state, the arm 120 may be in a flexible or articulating condition or state, and in the fixed or stabilizing state, the arm 120 may be in a rigid condition or state.

In some embodiments, each segment may be configured to change between a movable state and a fixed state. In some embodiments, each segment may be configured to compress and/or expand, e.g., with respect to at least the channel 102. As shown in FIG. 3, each stabilizing segment 130 may include one or more expandable members 132 and a plurality of the stabilizing particles (see, e.g., FIGS. 9A and B) disposed within each expandable member 132. In some embodiments, each expandable member 132 may be configured to change between compressed and released/expanded states based on gas (e.g., air) removed and supplied, respectively, for example, by a vacuum source. In some embodiments, each expandable member 132 may be any inflatable member, such as a balloon.

In some embodiments, the arm 120 may include one or more ports 134 disposed on the channel 102 at the location of each stabilizing segment 130 on the arm 120. Each of the ports 134 may be configured to cause the expanded state and the compressed state of each expandable member 132. Each port 134 may be configured to be an inlet and outlet for gas supplied, for example, by a vacuum source, to each stabilizing segment 130. The one or more ports 134 may be configured to communicate with the one or more internal channels configured to connect to a vacuum source. In this way, a vacuum source may be configured to control the state of the stabilizing segment(s) 130 and thereby control the state of the arm 120, for example, by delivering gas to and/or removing gas from each segment 130.

Figure 9A:
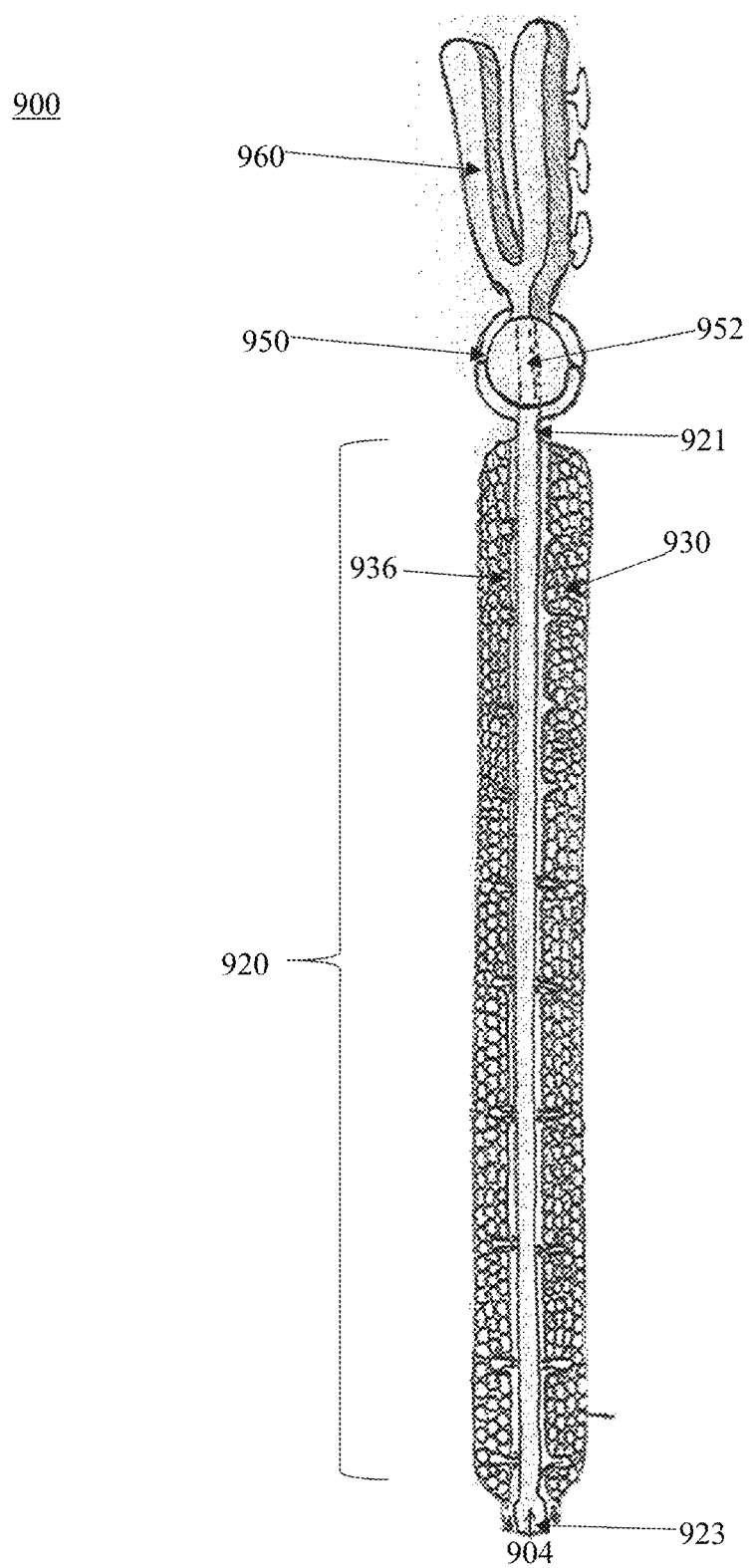
FIGS. 9A and B show a device for stabilizing tissue according to embodiments.
Figure 9B:
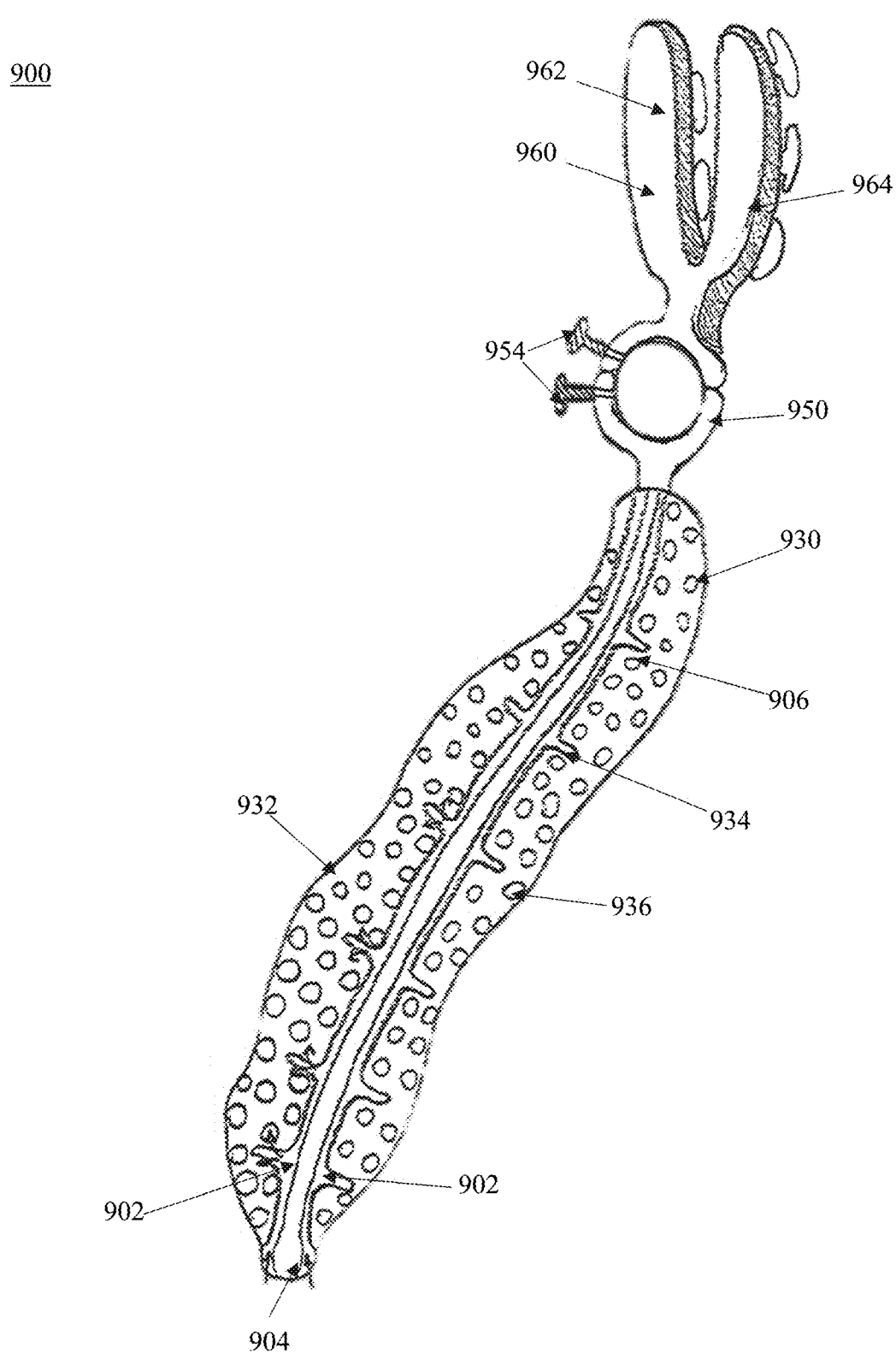

In some embodiments, the stabilizing particles may be made of a material, such as polystyrene or styrofoam. The stabilizing particles may be shaped and sized in a variety of geometries such as pellets, spheres, non-uniform shapes, or cylinders. In some embodiments, the size, shape and/or number of the stabilizing particles and/or the stabilizing segment 130 may depend on the amount of articulation and/or rigidity desired in the articulating condition and/or rigid condition. An example of the stabilizing particles are shown in FIGS. 9A and 9B.

In some embodiments, in the rigid or compressed state, the expandable members 132 compress the stabilizing particles against the channel 102 and therefore the stabilizing segment 130 may be in rigid or fixed state (e.g., harder to move the position of the arm/stabilizing segment (e.g., with respect to the member 160 and/or treatment area)). In the movable or flexible state, the one or more expandable members 132 are expanded (no longer compress against the channel 102) and the stabilizing particles are released within the member. When the stabilizing particles are released, there is a space between the stabilizing particles. In the expanded state, the stabilizing particles can move within the expandable member 132/segment 130 and therefore the stabilizing segment 130 may be in a movable or flexible state (e.g., easier to move the position of the arm/stabilizing segment (e.g., with respect to the member 160 and/or treatment area)).

In some embodiments, the arm 120 may include one or more articulating segments 140 disposed between the stabilizing segments 130. The one or more articulating segments 140 may include the exposed, outer surface of the one or more channels (e.g., the channel 102). There may be any number of articulating segments 140. In some embodiments, the one or more articulating segments 140 may be omitted, for example, if the stabilizing segment 130 extends the entire length of the arm 120 (e.g., see FIGS. 9A and B). If the device 100 includes one or more articulating segments 140, there may be one less than the number of stabilizing segments 130. For example, as shown in FIGS. 1 and 2, there may be three stabilizing segments and two articulating segments 140.

In some embodiments, the one or more articulating segments 140 and/or the stabilizing segments 130 may be disposed in an alternating pattern. In some embodiments, the one or more stabilizing segments 130 may be disposed to surround the channel 102 (e.g., cross-wise) along portions of the length and the one or more articulating segments 140 may be disposed there between, as shown in FIGS. 1 and 2. In other embodiments, the one or more stabilizing segments 130 and the one or more articulating segments 140 may extend along the length of the arm 120. For example, the one or more stabilizing segments 130 may appear to be ribs that extend along the length of the arm 120.

In some embodiments, the tissue stabilizing member 160 may have a U-shape, as shown in FIGS. 1, 2, 4 and 5. In other embodiments, the tissue stabilizing member 160 may have another shape, for example, a V-shape. In some embodiments, the tissue stabilizing member 160 may include two opposing segments 162 and 164. The opposing segments 162 and 164 may be configured to be moved independently. In some embodiments, the opposing segments 162 and 164 may be configured to be moved independently by a suspension system (not shown). By way of example, after the arm 120 and the tissue stabilizing member 160 are positioned and locked, the suspension system may be operated to move the segments 162 and/or 164 with respect to the treatment area.

Figure 4:
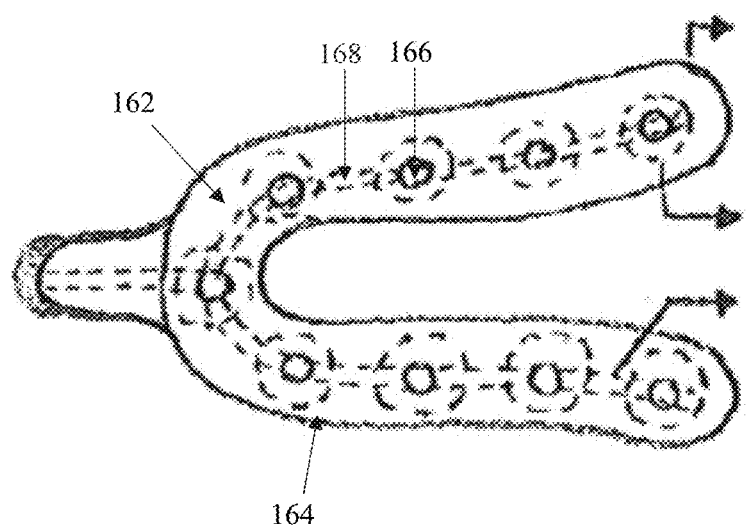
FIG. 4 shows the tissue stabilizing member shown in FIG. 1 according to embodiments.
Figure 5:
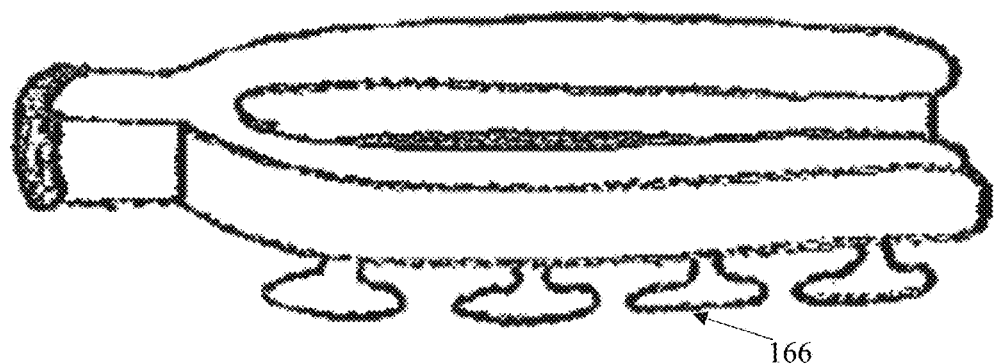
FIG. 5 shows another view of the tissue stabilizing member shown in FIG. 1 according to embodiments.

In some embodiments, the tissue stabilizing member 160 may include a plurality of contact members 166 disposed along the surface of the segments 162 and 164, as shown in FIGS. 4 and 5. The contact members 166 may be configured and dimensioned to contact the surface of tissue at a treatment area to stabilize the tissue and to facilitate the performance of a surgical procedure. In some embodiments, the contact members 166 may have a circular shape. In other embodiments, the contact members may have a different shape.

In some embodiments, the contact members 166 may be configured to engage tissue of the treatment area by application of suction, other mechanical means, or combinations thereof. In some embodiments, the segments 162, 164 may include at least one channel 168 that is in communication with the contact members 166 and configured to communicate with a vacuum source. By way of example, the contact members 166 may be configured to apply suction via the vacuum source connected to a vacuum connection disposed on the connection member 150 (e.g., a vacuum inlet) and/or connected to one of the channels of the arm 120 and delivered through the connection member 150. In some embodiments, the connection member 150 may include a valve configured to control the application of the suction.

FIGS. 9A and B show another example of a device according to some embodiments. FIGS. 9A and B show a tissue stabilizing device 900 that may include an articulating arm 920 having a first end 921, an opposing, second end 923, and a length there between. In some embodiments, the device 900 may include a tissue stabilizing member 960 disposed at the end 921 of the articulating arm 920. In some embodiments, the device 900 may include a handle member, including but not limited to the handle member 110 shown in FIG. 1, disposed at the end 923 of the articulating arm 920.

In some embodiments, the tissue stabilizing device 900 may include one or more channels or lumens that extends at least along the length of the at least the arm 920. In some embodiments, the one or more internal channels may be configured to communicate and/or connect to at least a vacuum source. In some embodiments, the channels may include a channel 904 that is configured to communicate with the tissue stabilizing member 960. The channel 904 extend at least from the end 923 to the tissue stabilizing member 960. The channel 904 may be configured to connect a vacuum source and/or deliver vacuum pressure from a vacuum source to the tissue stabilizing member 960. In some embodiment, the channels may include a channel 902 that surrounds the channel 904. The channel 902 may be configured to communicate with the articulating arm 920. The channel 902 may extend only the length of the arm 920. In some embodiments, the end 923 of the arm 920 may act as an inlet for the one or more channels (e.g., channels 902 and/or 904), for example, to at least the vacuum source and/or communicate with a vacuum source via a handle member.

In one embodiment, the device 900 may include one or more additional and/or alternative channels. For example, the device 900 may include one or more channels configured to receive a suspension configured to control the position of the arm 920 and/or the tissue stabilizing member 960 with respect to a handle member and/or the treatment area.

In some embodiments, the arm 920 may include one or more stabilizing segments 930 along the length of the arm. As shown in FIGS. 9A and 9B, the arm 920 may include one stabilizing segment 930 disposed along the length of the arm. In other embodiments, the arm 920 may include more than one stabilizing segments 930. In some embodiments, each stabilizing segment 930 may include one or more expandable members 932 and a plurality of stabilizing particles 936 disposed within each expandable member 932/stabilizing segment 930. The one or more expandable members 932 may be configured to change between an expanded state and a compressed state. In this example, the stabilizing segment 930 may include one continuous expandable member 932. In some embodiments, the expandable member 132 may be configured to expand and compress based on gas (e.g., air) supplied, for example, by a vacuum source. The expandable member 132 may be any inflatable member, such as a balloon.

In some embodiments, the one or more stabilizing segments 930 may be configured to change between a movable or flexible state and a fixed or stabilizing state, for example, based on the state of the expandable members. FIG. 9A shows the one or more stabilizing segments 930 in the stabilizing state (i.e., the expandable member compressed with respect to the channel 902) and FIG. 9B shows the one or more stabilizing members in a flexible state (i.e., the expandable member expanded or released with respect to the channel 902). When the one or more segments 930 are in the flexible or movable state, the arm 920 may be in a flexible or articulating condition or state, and when the one or more segments 930 are in the stabilizing state, the arm 920 may be in a rigid condition or state.

In some embodiments, the arm 920 may include one or more ports 934 disposed and/or communicates with the channel 902. Each of the ports 934 may be configured to cause the expanded state and the compressed state of each expandable member 932. As shown in FIGS. 9A and 9B, the arm 920 includes a plurality of spaced ports. Each port 934 may be configured to be an inlet and outlet for gas supplied, for example, by a vacuum source, to each stabilizing segment 930 via the channel 904. In this way, a vacuum source may be configured to control the state of the stabilizing segment(s) 930 and thereby control the state of the arm 920, for example, by delivering gas to the segment 930, which will cause the segment 930 to expand/release with respect to the channel 902, and/or remove gas from the segment 930, which will cause the segment 930 to compress against the channel 902.

In some embodiments, like the stabilizing particles discussed with respect to FIGS. 1-3, the stabilizing particles 936 may be made of a material, such as polystyrene or styrofoam. The stabilizing particles 936 may be shaped and sized in a variety of geometries such as pellets, spheres, non-uniform shapes, or cylinders. In some embodiments, the size, shape and/or number of the stabilizing particles 936 and/or the stabilizing segment 930 may depend on the amount of articulation and/or rigidity desired in the articulating condition and/or rigid condition.

In some embodiments, like the device 100, in the fixed or rigid state, the one or more expandable members 932 may be in the compressed state. In the compressed state, the stabilizing particles 936 are compressed against the channels 902/904 and therefore the stabilizing segment 930 may be in rigid or fixed state (e.g., hard to move the position of the arm/stabilizing segment). In the flexible or movable state, the one or more expandable members 932 may be in the expanded or released state. In the expanded state, the stabilizing particles 936 are released and can move within the segment 930, and therefore the stabilizing segment 930 may be in a flexible or movable state (e.g., easier to move the position of the arm/stabilizing segment).

In some embodiments, the tissue stabilizing member 960 may have a U-shape, like the member 160 shown in FIGS. 1, 2, 4 and 5. In other embodiments, the tissue stabilizing member 960 may have another shape, for example, a V-shape. In some embodiments, the tissue stabilizing member 960 may include two opposing segments 962 and 964. The opposing segments 962 and 964 may be configured to be moved independently. In some embodiments, the opposing segments 962 and 964 may be configured to be moved independently by a suspension system (not shown). By way of example, after the arm 920 and the tissue stabilizing member 960 are positioned and locked, the suspension system may be operated to move the segments 962 and/or 964 with respect to the treatment area.

In some embodiments, the tissue stabilizing member 960 may include a plurality of contact members 966 disposed along the surface of the segments 962 and 964. The contact members 166 may be configured and dimensioned to contact the surface of tissue at a treatment area to stabilize the tissue and to facilitate the performance of a surgical procedure. In some embodiments, the contact members 966 may have a circular shape. In other embodiments, the contact members may have a different shape.

In some embodiments, the contact members 966 may be configured to engage tissue of the treatment area by application of suction, other mechanical means, or combinations thereof, for example, through the channel 904. In some embodiments, the segments 962, 964 may include at least one channel that is in communication with the contact members 966 and the channel 904.

In some embodiments, the device 900 may include a connection member 950 that is disposed between and connects the tissue stabilizing member 960 and the arm 920. The connection member 950 may be configured to allow rotation of each of the tissue stabilizing member 960 and the arm 920 with respect to the connection member 950. In some embodiments, the connection member 950 may include but is not limited to a ball and socket joint. In some embodiments, the member 950 may include a first section (e.g., hemisphere) that is attached to the arm 920, a second section (e.g., hemisphere) that is attached to the member 960, and a rotation member (e.g., ball) disposed inside and between the first and second sections and that is configured to rotate between the sections.

In some embodiments, the device 900 may include a locking member 954 disposed on the connection member 950 that is configured to independently lock the position of the tissue stabilizing member 960 and the position of the articulating arm 920 with respect to the connection member 950. For example, the locking member 954 may be configured to lock the position of each of the first section and the second section with respect to the rotation member so as to prevent rotation of the member 960 and/or arm 920 with respect to the connection member 950 and/or treatment area (e.g., when a desired configuration/position is determined). The locking member 954 may include but is not limited to two screws, a first screw to lock the position of the tissue stabilizing member 960 with respect to the connection member 950 and a second screw to lock the position of the articulating arm 920 with respect to the connection member 950.

In some embodiments, the connection member 950 may include a channel 952 that communicates to the channels of the segments 962 and 964 and the channels 902 and/or 904. By way of example, the contact members 966 may be configured to apply suction via the vacuum source connected to the channel 904. For example, the channel 904 may include a vacuum connection (e.g., a valve) disposed at the end 923.

Figure 6:
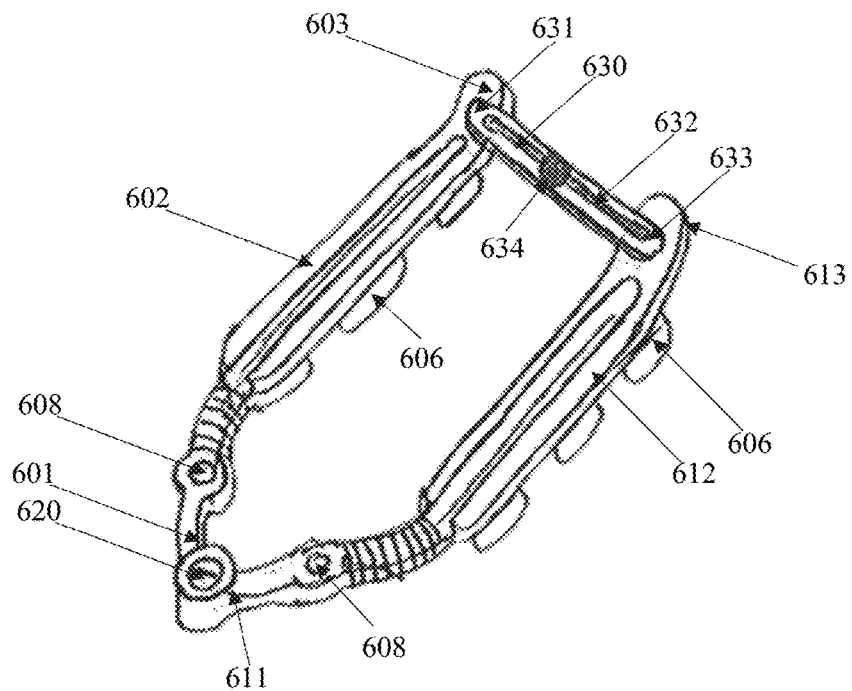
FIG. 6 shows a tissue stabilizing member according to embodiments.
Figure 7:
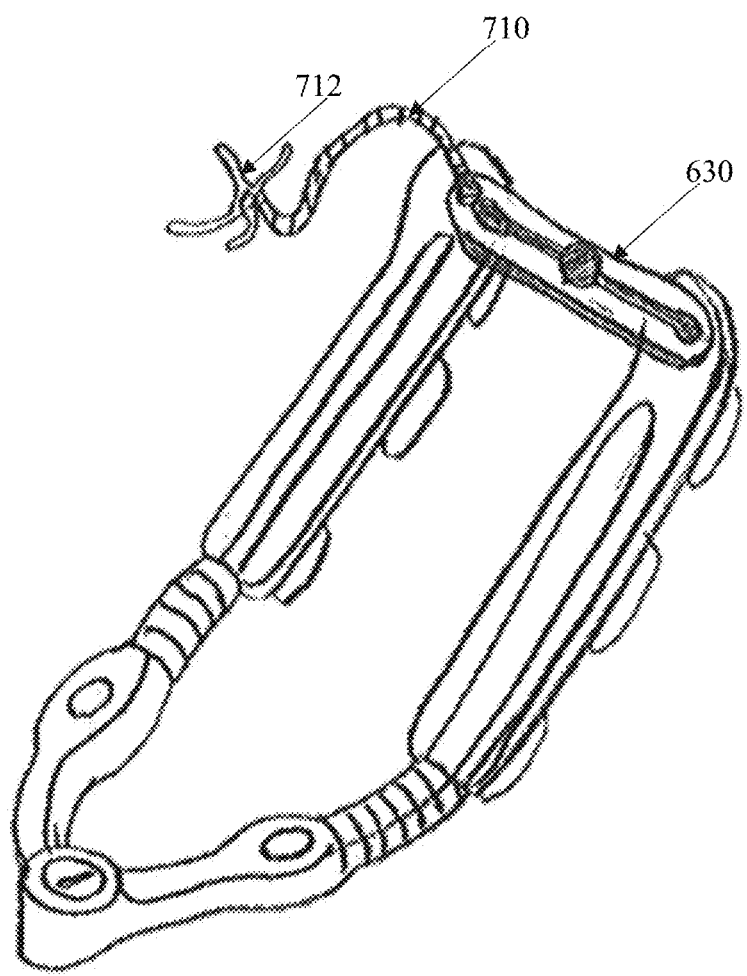
FIG. 7 shows another view of the tissue stabilizing member shown in FIG. 6 according to embodiments.

FIGS. 6 and 7 show a tissue stabilizing member 600 according to some embodiments. In some embodiments, a device, that may include but is not limited to the device 100 and/or the device 900, as well as other devices, may include the tissue stabilizing member 600.

In some embodiments, the tissue stabilizer member 600 may include two segments 602 and 612. The first segment 602 may have a first end 601, an opposing second end 603 and a length there between. The second segment 612 may have a first end 611, a second end 613 and a length there between. Like the tissue stabilizing member 160, each of the segments 602, 612 may include a plurality of contact members 606 disposed along the length and at least one channel that is in communication with the contact members 606 and configured to communicate with a vacuum source. In some embodiments, each of the segments 602, 612 may include at least one vacuum connection 608 configured to connect to a vacuum source. In some embodiments, the vacuum connection 608 may be disposed near one end of each segment. Each vacuum connection 608 may include a valve configured to control the application of the suction. For example, like the contact members 166, the contact members 606 may be configured to apply suction via the vacuum source connected to the vacuum connection 608 (e.g., a vacuum inlet).

In some embodiments, the first end 601 of the first segment 602 and the first end 611 of the second segment 612 may converge at a point. In some embodiments, the first end 601 and the first end 612 may be connected to each other via a hinge 620. The hinge 620 may be configured to allow swiveling motion of each segment. In some embodiments, the tissue stabilizer member 600 may include a stretching member 630 that is disposed across and attached to the second ends 604, 613 of the segments. In some embodiments, the stretching member 630 may be configured to stretch the tissue, for example, the coronary tissue that the contact members 606 engage. In some embodiments, the stretching member 630 may include a first end 631, a second end 633 and a length there between. In some embodiments, the stretching member 630 may include a channel 632 disposed along the length and a sliding member 634 that slides within the channel 632. The length of the stretching member 630 may be configured to increase or decrease by moving the sliding member 634 along the channel By moving the sliding member 634 to cause the length of the stretching member 630 to increase or expand, the distance between the second end of the segments 602 and 612 may also increase and thereby cause stretching of any tissue engaged by the contact members 666. By way of example, the tissue stabilizing member 600 can stretch an incision coronary tissue to better enable suturing of a graft.

In some embodiments, the tissue stabilizer member 600 may include a graft mounting device 710 having one end disposed on the stretching member 630 and the opposing end including a graft mounting member 712, as shown in FIG. 7. The graft mounting member 712 may be configured to removably engage a graft for implantation, for example, in coronary tissue. The graft mounting member 712 may include but is not limited to spaced apart prongs.

Figure 8A:
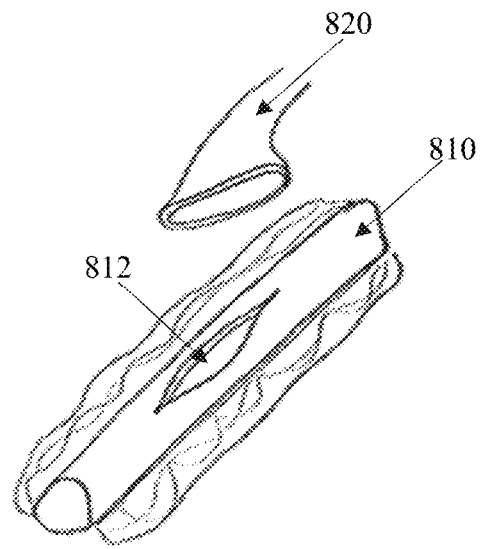
FIGS. 8A-D shows a method of using the device having the tissue stabilizing member shown in FIG. 6 according to embodiments.
Figure 8B:
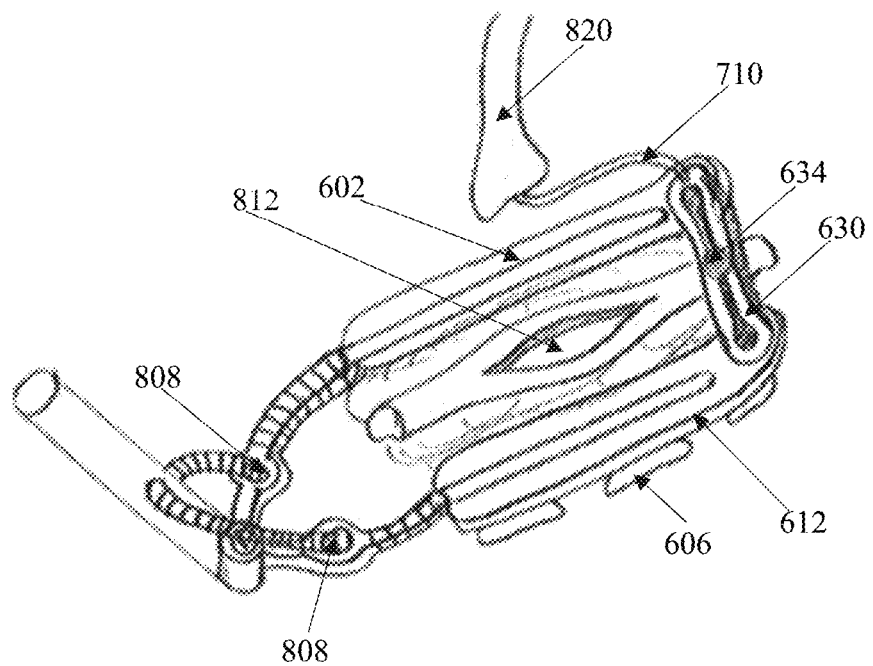
Figure 8C:
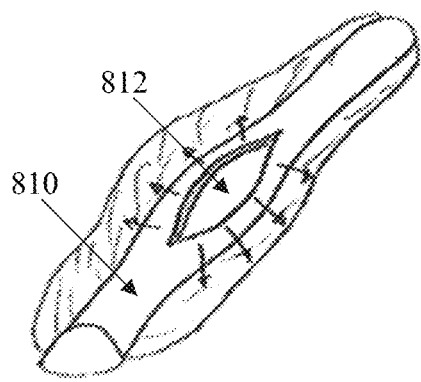
Figure 8D:
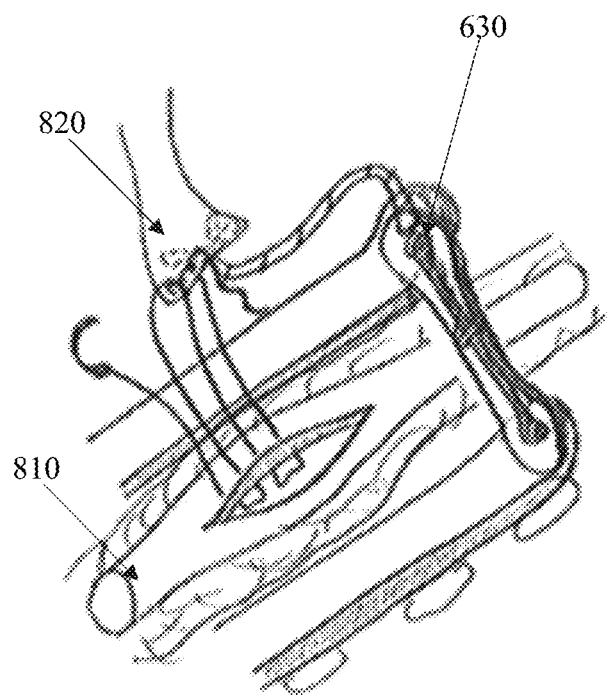

FIGS. 8A-D illustrates an example using the tissue stabilizing member 600 to stretch coronary tissue for placement of a graft. FIG. 8A shows an incision 812 in coronary tissue 810 for placement of a graft 820. To prepare for placement, the graft 820 may be mounted on to the graft mounting member 712 disposed on the tissue stabilizing member 630. As shown in FIG. 8B, after the incision 812 is placed in the coronary tissue 810, the tissue stabilizing member 600 with the graft 820 may be positioned on the coronary tissue to surround the incision 812. As shown in FIG. 8B, the segments 602 and 606 are disposed on either sides of the coronary incision 812 and the stretching member 630 is disposed perpendicular to the incision 812. In this placement, the contact members 606 may engage the tissue adjacent to the coronary incision 812. After the contact members 606 are placed on the tissue adjacent to the coronary incision 812, vacuum pressure may be delivered from a vacuum source via the vacuum connections 608 to the contact members 606 so that the surrounding coronary tissue is held by the contact members 606. After which, the sliding member 634 may be moved so as to increase the length of the stretching member 630, thereby causing the segments 602 and 606 to move further away from each other causing the coronary incision 812 to stretch, as shown in FIG. 8C. After the coronary incision 812 is stretched to the desired point by the tissue stabilizing member 600, the graft 820 may be sutured to the tissue 810 at incision 812, as shown in FIG. 8D.

According to some embodiments, one, some or all components of the devices may be structured for single use or be disposable. In some embodiments, one, some or all components may be sterilized. According to some embodiments, a portion or combination of the single use items may be sold as kit.

While various embodiments of the disclosure have been described, the description is intended to be exemplary rather than limiting and it will be appeared to those of ordinary skill in the art that may more embodiments and implementations are possible that are within the scope of the disclosure.

What is claimed:

1. A device for stabilizing tissue, comprising:
   an articulating arm having a first end, a second end, and a length there between;
   one or more channels disposed along at least the length of the articulating arm, the one or more channels including an internal channel disposed along at least the length of the articulating arm;
   one or more stabilizing segments disposed along at least a portion of the length of the articulating arm, each stabilizing segment being configured to compress and expand with respect to the internal channel;
   a plurality of ports disposed on the internal channel within each stabilizing segment; and
   a tissue stabilizing member disposed at the second end of the articulating arm,
   wherein:
      the articulating arm is configured to move between a fixed state and movable state based on a state of the one or more stabilizing segments;
      in the fixed state, the one or more stabilizing segments is compressed against the internal channel, and
      in the movable state, the one or more stabilizing segments are expanded with respect to the internal channel.

2. The device according to claim 1, further comprising:
   a plurality of stabilizing particles disposed within each stabilizing segment,
   wherein in the fixed state, the one or more stabilizing particles are compressed against the internal channel by the one or more stabilizing segments, and
   wherein in the movable state, the one or more stabilizing particles are released within each stabilizing segment with respect to the internal channel.

3. The device according to claim 2, wherein the internal channel is configured to communicate with a source to deliver and/or remove a gas to respectively expand and/or compress each stabilizing segment through the plurality of ports.

4. The device according to claim 1, further comprising:
   one or more articulating segments disposed between the one or more stabilizing segments along the length of the articulating arm,
   wherein the one or more articulating segments and the stabilizing segments are disposed along a portion of the length of the articulating arm and are disposed to surround the internal channel.

5. The device according to claim 4, wherein the one or more articulating segments and the stabilizing segments are disposed in an alternating pattern.

6. The device according to claim 5, wherein the tissue stabilizing member includes a first segment and an opposing second segment, the first segment and the second segment being configured to be moved independently.

7. The device according to claim 6, wherein the first and second segments include a plurality of tissue contact members.

8. The device according to claim 1, further comprising:
   a connection member disposed between the articulating arm and the tissue stabilizing member, the tissue stabilizing member and the articulating arm being configured to rotate independently with respect to the connection member.

9. The device according to claim 1, wherein each stabilizing segment includes one or more expandable members configured to expand and compress with respect to the internal channel.

10. The device according to claim 1, further comprising:
    a handle member disposed at the second end of the articulating arm.

11. A device for stabilizing tissue, comprising:
    an articulating arm having a first end, a second end, and a length there between;

one or more channels disposed along at least the length of the articulating arm, the one or more channels including an internal channel disposed along at least the length of the articulating arm;

one or more stabilizing segments disposed along at least a portion of the length of the articulating arm, each stabilizing segment being configured to compress and expand with respect to the internal channel;

a plurality of stabilizing particles disposed within each stabilizing segment; and a tissue stabilizing member disposed at the second end, wherein:

the articulating arm is configured to move between a fixed state and movable state based on a state of the one or more stabilizing segments;

wherein in the fixed state, the one or more stabilizing particles are compressed against the internal channel by the one or more stabilizing segments, and wherein in the movable state, the one or more stabilizing particles are released within each stabilizing segment by the one or more stabilizing segments being expanded with respect to the internal channel.

12. The device according to claim 11, further comprising:

a plurality of ports disposed along the internal channel within each stabilizing segment and configured to deliver and/or remove a gas to each stabilizing segment, wherein the internal channel is configured to communicate with a source to deliver and/or remove a gas to respectively expand and/or compress each stabilizing segment through the plurality of ports.

13. The device according to claim 11, further comprising:

one or more articulating segments disposed between the one or more stabilizing segments along the length of the articulating arm, wherein the one or more articulating segments and the stabilizing segments are disposed along a portion of the length of the articulating arm and are disposed to surround the internal channel.

14. The device according to claim 13, wherein the one or more articulating segments and the stabilizing segments are disposed in an alternating pattern.

15. The device according to claim 14, wherein the tissue stabilizing member includes a first segment and an opposing second segment, the first segment and the second segment being configured to be moved independently.

16. The device according to claim 11, further comprising:

a connection member disposed between the articulating arm and the tissue stabilizing member, the tissue stabilizing member and the articulating arm being configured to rotate independently with respect to the connection member.

17. The device of claim 16, the device further comprising:

a locking member disposed on the connection member and configured to independently lock a position of the tissue stabilizing member and a position of the articulating arm with respect to the connection member.

18. The device according to claim 16, wherein the connection member includes one or more channels that communicates with the one or channels of the articulating arm.

19. The device according to claim 11, wherein each stabilizing segment includes one or more expandable members configured to expand and compress with respect to the internal channel.

20. The device according to claim 11, further comprising:

a handle member disposed at the second end of the articulating arm.

* * * * *